United States Patent
Boyer et al.

(10) Patent No.: US 7,244,849 B2
(45) Date of Patent: Jul. 17, 2007

(54) PROCESS FOR PREPARING A THIAZOLE PPAR-LIGAND AND POLYMORPHS THEREOF

(75) Inventors: Thierry Boyer, Les Ulis (FR); Caroline Jane Day, Stevenage (GB); Andrew Jonathan Whitehead, Stevenage (GB); Richard Anthony Henson, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 535 days.

(21) Appl. No.: 10/478,260

(22) PCT Filed: May 29, 2002

(86) PCT No.: PCT/EP02/05884

§ 371 (c)(1),
(2), (4) Date: Apr. 27, 2004

(87) PCT Pub. No.: WO02/096893

PCT Pub. Date: Dec. 5, 2002

(65) Prior Publication Data

US 2004/0242657 A1   Dec. 2, 2004

(30) Foreign Application Priority Data

May 31, 2001 (GB) ................... 0113232.3

(51) Int. Cl.
*C07D 277/20* (2006.01)
(52) U.S. Cl. .................... 548/200; 548/146
(58) Field of Classification Search ........... 548/146, 548/200
See application file for complete search history.

(56) References Cited

U.S. PATENT DOCUMENTS

| 6,518,290 B1 * | 2/2003 | Sierra ............ 514/365 |
| 6,867,225 B2 * | 3/2005 | Dumaitre et al. ...... 514/365 |
| 7,091,225 B2 * | 8/2006 | Sierra ............ 514/365 |
| 7,091,237 B2 * | 8/2006 | Beswick et al. ........ 514/438 |

FOREIGN PATENT DOCUMENTS

| EP | 1 067 109 | 1/2001 |
| WO | WO 01 40207 | 6/2001 |

OTHER PUBLICATIONS

Randad, R.S., et al. "Allosteric modifiers of hemoglobin. 1. Design, synthesis, testing, and structure-allosteric activity relationship of novel hemoglobin oxygen affinity decreasing agents." Journal of Medicinal Chemistry, vol. 34, No. 2, Feb. 1991, pp. 752-757.

* cited by examiner

*Primary Examiner*—Golam M. M. Shameem
(74) *Attorney, Agent, or Firm*—Jennifer L. Fox

(57) ABSTRACT

A method of preparing a compound of formula (I), and pharmaceutically acceptable salts and solvates thereof. Polymorphs of this compound and their use as PPAR ligands are also disclosed 1 Claim, 3 Drawing Sheets

PROCESS FOR PREPARING A THIAZOLE PPAR-LIGAND AND POLYMORPHS THEREOF

This application is filed pursuant to 35 U.S.C. § 371 as a United States National Phase Application of International Application No. PCT/EP02/05884 filed May 29, 2002, which claims priority from GB 0113232.3 filed May 31, 2001.

FIELD OF THE INVENTION

The present invention relates to a process for the synthesis of the human peroxisome proliferator activated receptor (PPAR) alpha activator 2-methyl-2-[4-{[(4-methyl-2-[4-trifluoromethylphenyl]thiazol-5-yl-carbonyl)amino]methyl}phenoxy]propionic acid. The invention also relates to particular polymorphs of this compound, methods of making them, pharmaceutical compositions containing them and their use in therapy.

BACKGROUND TO THE INVENTION

Peroxisome Proliferator Activated Receptors (PPARs) are orphan receptors belonging to the steroid/retinoid receptor superfamily of ligand-activated transcription factors. See, for example, Willson, T. M. and Wahli, W., *Curr. Opin. Chem. Biol.*, (1997), Vol. 1, pp 235-241.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endocrin. Met* 291-296,4 (1993)).

Certain compounds that activate or otherwise interact with one or more of the PPARs have been implicated in the regulation of triglyceride and cholesterol levels in animal models. See, for example, U.S. Pat. No. 5,847,008 (Doebber et al and U.S. Pat. No. 5,859,051 (Adams et al.) and PCT publications WO 97/28149 (Leibowitz et al.) and WO99/04815 (Shimokawa et al.).

WO 01/40207 describes novel compounds having the following general formula and pharmaceutically acceptable salts, solvates and hydrolysable esters thereof:

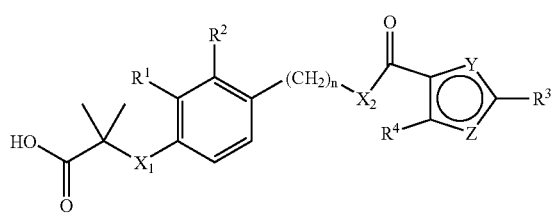

Wherein;
$X_1$ represents O or S;
$R^1$ and $R^2$ independently represent H, halogen, —$CH_3$ and —$OCH_3$;
n represents 1 or 2;
$X_2$ represents NH, $NCH_3$ or O;
One of Y and Z is N, and the other is O or S;

$R^3$ represents phenyl or pyridyl (wherein the N is in position 2 or 3) and is optionally substituted by one or more halogen, $NO_2$, $NH_2$, $CF_3$, $OCF_3$, $OC_{1-6}$ straight or branched alkyl, $C_{1-6}$ straight or branched alkyl, alkenyl or alkynyl with the provision that when $R^3$ is pyridyl, the N is unsubstituted;
$R^4$ represents $CF_3$ or $CH_3$.

These compounds are agonists of hPPAR alpha and have utility in treatment of diseases or conditions mediated by hPPAR alpha.

WO 01/40207 describes the routes by which the above compounds may be prepared. The compounds may be conveniently prepared by a general process (I) wherein a moiety like (A) is coupled to an acid (B) using a peptide coupling reaction or by acylation of (A) using a suitable non nucleophilic amine with an acid chloride (C). Preferably, R is $C_{1-6}$ alkyl which can be hydrolyzed off to give an acid of the above compound, or if readily hydrolyzable, the resulting ester can be administered.

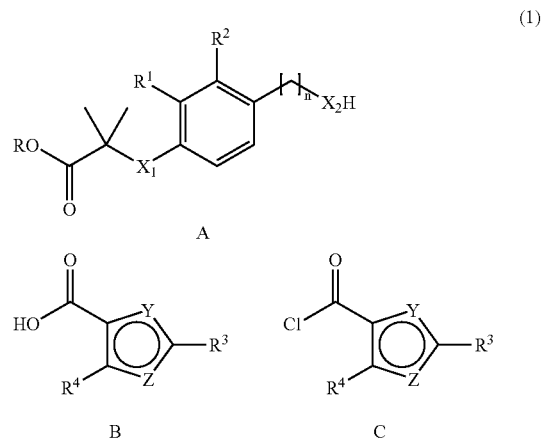

Alternatively, the compounds may be prepared by a second method in which compounds of formula (D) are reacted with ethyl 2-bromo-2 methyl propionate to produce the ethyl ester of the compound which then may then be hydrolysed to produce the free acid.

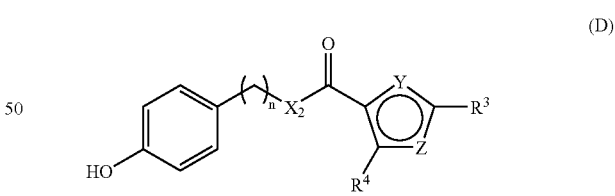

Compounds of formula (D) may be prepared from the reaction between compounds of formula (B) and compounds of formula (E) with $HOBT/EDC/NEt_3$ when $X_2$ is NH or $NCH_3$ or $DIC/DMAP/NEt_3$ when $X_2$ is O.

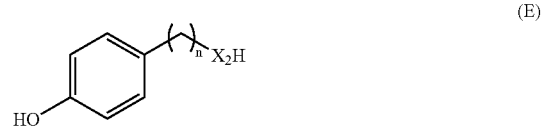

A particularly preferred compound described in WO 01/40207 is 2-methyl-2-[4-{[4-methyl-2-[4-trifluoromethylphenyl]thiazol-5-yl-carbonyl)amino]methyl}phenoxy] propionic acid and salts, solvates and hydrolysable esters thereof.

The synthesis of this compound in WO 01/40207 follows the two general methods described above. For general method (I), R in moiety (A) represented ethyl.

The present inventors have found that synthesis of this compound by the former method (I), wherein R represents H or methyl is advantageous over the previously exemplified route wherein R is ethyl.

SUMMARY OF THE INVENTION

According to a first aspect of the invention there is provided a method of preparing a compound of formula (I).

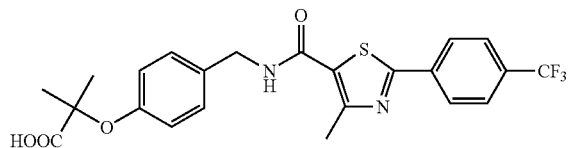

(I)

and pharmaceutically acceptable salts and solvates thereof comprising the reaction of a compound of formula (II)

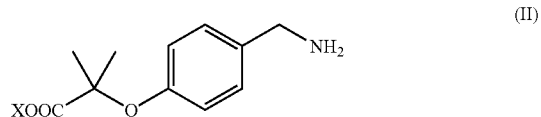

(II)

wherein X is Me or H
with a compound of formula (III)

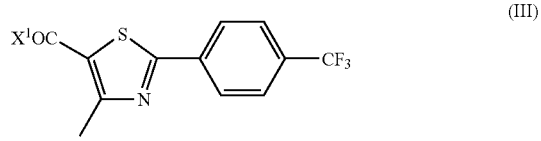

(III)

wherein $X^1$ is chlorine or imidazole.
Preferably $X^1$ is chlorine

According to a second aspect of the invention there are provided particular polymorphs of the compound of formula (I). These may be prepared by routes described in WO 01/40207 and more especially by the specific routes described herein. Particular polymorphs are described hereinafter and are defined as "form 2" and "form 6". These polymorphs may be defined by e.g. reference to the X-Ray Diffraction (XRD) and specific melting point. In addition hydrates and alcohol solvates have also been identified. These polymorphic forms are hereinafter referred to as "compounds of the invention".

In another aspect, the present invention provides pharmaceutical compositions comprising the compounds of the invention, preferably in association with a pharmaceutically acceptable diluent or carrier.

In another aspect, the present invention provides the compounds of the invention for use in therapy, and in particular, the human medicine.

In another aspect, the present invention provides the use of one or more of the compounds of the invention for the manufacture of a medicament for the treatment of a hPPAR alpha mediated disease or condition.

In another aspect, the present invention provides a method of treatment of a patient suffering from a hPPAR alpha mediated disease or condition comprising the administration of a therapeutically effective amount of one or more of the compounds of the invention.

As used herein the compounds of the invention also includes pharmaceutically acceptable salts or solvates or hydrolyzable esters thereof.

DETAILED DESCRIPTION OF THE INVENTION

Figure 1:
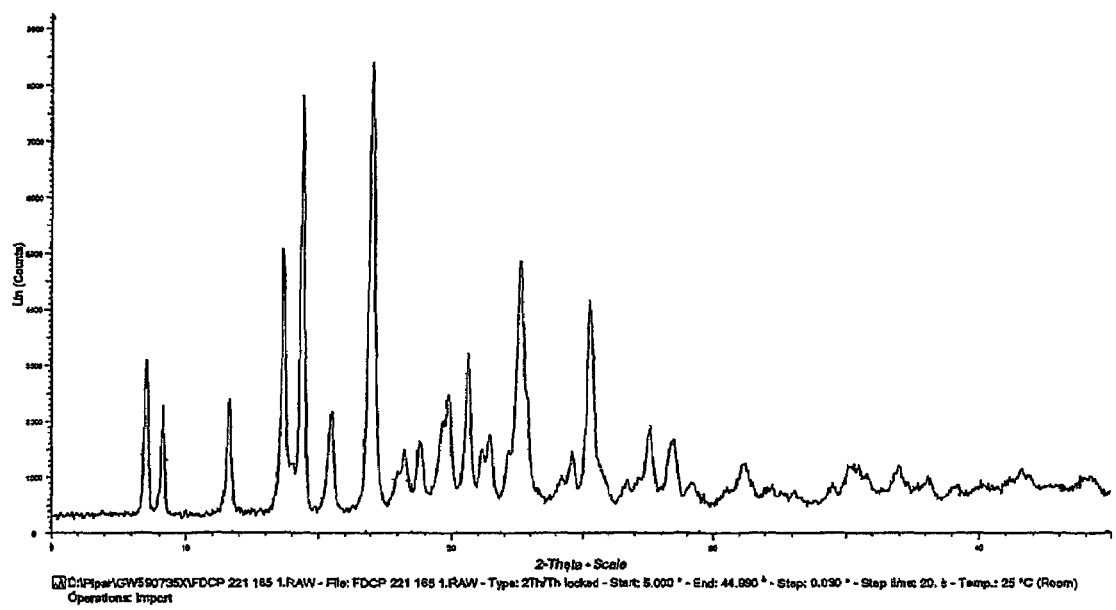
FIG. 1: XRD diagram of form 2 of 2-methyl-2-[4-{[4-methyl-2-[4-trifluoromethylphenyl]thiazol-5-yl-carbonyl) amino]methyl}phenoxy]propionic acid.

The first aspect of the invention provides methods of preparing a compound of formula (I). These methods provide advantages over the specific disclosures of methods of preparing this compound described in WO 01/40207 in that when R is H the method of the present invention is shorter, and when R is H or Me all the intermediates may be isolated as solids which confers significant advantages during processing. The use of protecting groups and toxic reagents for synthesis of compound of formula (A) above where R is Me or H is also minimised.

Compounds of formula (II) may be reacted with compounds of formula (III) under suitable reaction conditions. Compounds of formula (II) where X=Me or H may couple directly to compounds of formula (III) where $X^1$=imidazole or chlorine.

For example, when X=Me the compound of formula (III) where $X^1$=chlorine (1.15 eq) was dissolved in DCM and triethylamine (1.2 eq) was added. This solution was cooled to 2° C., and a solution of the compound of formula (II) with X=Me (1 wt) in DCM was added dropwise maintaining the temperature at 2±3° C. This mixture was then stirred for 30 min at 2±2° C. before warming to room temperature. When the reaction was complete by HPLC the reaction mixture was quenched with water, and the biphasic solution was separated. The organics were then sequentially washed with 1 N aq HCl, water, 5% w/v aq $K_2CO_3$, and water, before being concentrated in vacuo to a low volume. The product was isolated as a crystalline solid by the addition of iso-octane and reconcentration. Expected Yield: 78% theory, 125% w/w.

In a further example, when X=H the compound of formula (II) where X=H (1.2 eq) was suspended in DCM and triethylamine (1.3 eq) was added. Stirred for 1 hr at room temp, then treated with the solution of compound of formula (III) with X=imidazole. The mixture was stirred for 3-5 hrs at room temp, then quenched with 2M aq HCl. The biphasic mixture was separated, and the organic phase was washed with 2M HCl and then water. After concentration in vacuo to a low volume, the mixture was diluted with ethyl acetate and filtered. The product was isolated by crystallisation from ethyl acetate/iso-octane. Expected yield 50-55% theory.

When X=Me the coupled product may be hydrolysed to give the compound of formula (I) using methods apparent to a skilled person, For example, the coupled product where X=Me (1 wt) was suspended in 1:1 methanol and water, and to this mixture was added solid NaOH (1.1 eq). The resulting slurry was heated to 65° C. and held thus for 120 min, by which time a complete, pale yellow solution had formed, and the reaction was sampled for analysis by HPLC.

Once complete, the reaction mixture was cooled to 20° C., and then concentrated in vacuo to ca 3.5 vols. This solution was extracted with DCM, and the organics were discarded. The aqueous solution was overlain with ethyl acetate (5 vol) and stirred vigorously whilst a solution of aqueous HCl (2M, 3 vol) was added slowly over 10 mins, to give a final aqueous pH of 1. The resultant biphasic solution was then separated, and the aqueous was further extracted with ethyl acetate before being discarded. The organic liquor was then concentrated in vacuo to ca 3 vol and a series of dilutions reconcentrations performed to dry the ethyl acetate. (I) was obtained described in the examples.

The compound of formula (III) wherein $X^1$ is chlorine or imidazole may be prepared from compounds of formula (IV) by reaction in a suitable solvent with thionyl chloride ($X^1$ is chlorine) or 1,1'-carbonyldiimidazole ($X^1$ is imidazole):

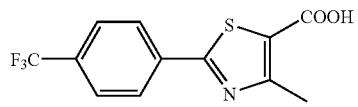

(IV)

For example, when $X^1$ is chlorine the compound of formula (IV) was suspended in EtOAc and this slurry was heated to 72° C. with stirring under nitrogen. Thionyl chloride (1.50 eq) was then added dropwise and the resulting mixture was allowed to reflux until complete by HPLC monitoring. The batch was cooled back to 20° C. The batch was then concentrated in vacuo to a low volume and diluted with iso-octane. This process was repeated twice more before cooling to 20°. The product (compound of formula (III)) was then collected by vacuum filtration and washed with iso-octane. Expected Yield: 83% theory, 91% w/w. For example when $X^1$ is imidazole the compound of formula (IV) (1 wt) was suspended in DCM and CDI (1.3 eq) is added. This mixture was stirred for 2-3 hrs at room temp to obtain a complete solution, which can be used directly in the next stage.

Compounds of formula (IV) may be prepared from a compound of formula (V):

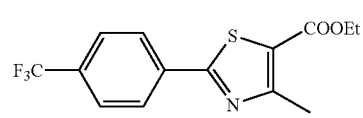

(V)

by techniques apparent to a skilled person. Particular reaction conditions are:

To the compound (V) (1.84 g, 5.8 mmol) in THF was added 1 N LiOH (6 mL, 6 mmol) and the reaction stirred at rt. After ~3 h, the reaction was neutralized with 1N HCl, extracted 3×100 mL EtOAc, dried over $Na_2SO_4$, filtered and the solvent removed under vacuum to afford 1.5 g (89%) Compound (IV) as a white solid. 1H NMR (DMSO-d6): δ 13.55 (bs, 1H), 8.25 (d, 2H), 7.95 (d, 2H), 2.75 (s, 3H).

Compound (V) may be prepared from a compound (VI)

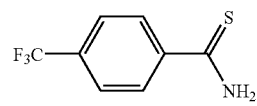

(VI)

Suitable reaction conditions will be apparent to the skilled person. Particularly a solution of ethyl 2-chloroacetoacetate (35.4 g, 29.7 mL, 0.21 mol) and 4-(trifluoromethyl)thiobenzamide (VI) (44 g, 0.21 mol) in EtOH (300 mL) was refluxed overnight. After cooling to room temperature the solvent was removed in vacuo.

The compound of formula (VI) is commercially available.

Compound of formula (II) wherein X is methyl is conveniently prepared from compound (VII):

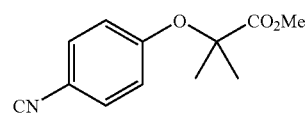

(VII)

Suitable reaction conditions for X=Me are: (vii) (1 wt) was dissolved in IMS and AcOH with stirring at 20° C. Hydrogenation catalyst (10% Pd/C, 50% wet, 0.075 wt) was added, the mixture was purged with hydrogen, and then stirred vigorously under hydrogen at atmospheric pressure for 135±30 mins until complete (Monitored by hydrogen uptake and/or HPLC). The reaction mixture was purged with nitrogen, and filtered through a pad of dry filter aid to remove catalyst, the cake was washed through with isopropyl acetate, and the filtrate and wash was combined. The organic liquor was concentrated in vacuo to a low volume, and isopropyl acetate was added. Reconcentrated in vacuo to low volume, then isopropyl acetate and water were sequentially added. This mixture was then shaken to give a complete biphasic solution, which was separated and the organics were discarded. The aqueous was treated with conc HCl, and extracted with isopropyl acetate. The organics were discarded, and the aqueous was treated with 32% NaOH dropwise. This solution was then added dropwise to a stirred slurry of $K_2CO_3$ (1 wt) in DCM, and this mixture was stirred vigorously to obtain a complete biphasic solution. The two phases were then separated and the aqueous phase was extracted again with DCM. The DCM extracts were combined and concentrated atmospherically to a low volume, rediluted with DCM and concentrated to ca 5 vols. This solution was used directly in the next stage. Expected Yield: 83% theory, 84% w/w.

This compound (VII) has not been reported in the literature and is thus believed to be novel. This compound forms a further feature of the invention:

The compound (VII) and compound of formula (II) where X is H are prepared from compound (VIII)

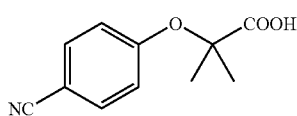
(VIII)

Suitable reaction conditions are: 2-(4-cyanophenoxy)-2-methylpropionic acid (or compound (viii)) (1 wt) was dissolved in methanol and trimethylorthoformate (TMOF, 1 vol) with stirring under nitrogen[1]. Sulfuric acid (98%, 0.08 vol, 0.32 eq) was then added, and the mixture was heated to reflux with HPLC monitoring. The reaction was typically complete after approx 1.5-2 hrs at reflux. The batch was cooled, and added to a stirred suspension of potassium carbonate (0.65 eq) in isopropyl acetate and then concentrated in vacuo to a total volume of approx 4 vol. Isopropyl acetate was added, and the slurry concentrated in vacuo to a total volume of approx 4 vol. Isopropyl acetate (4 vol) and water (5 vol) was added, the resultant biphasic solution was separated, and the organics were washed with water. The product was obtained by crystallisation from isopropylacetate/iso-octane with seeding. Expected yield: 93% theory, 99% w/w. Suitable reaction conditions for compound of formula (II) where X is H are: The compound (vii) is suspended in IMS containing AcOH, and treated with 10% Pd/C catalyst (50% wet, 0.1 wt). Hydrogenated at room temp for 60-90 mins until essentially complete by HPLC. The aminoacid precipitates during the reduction to give a fairly thick slurry at the end of the reaction. This is diluted with water and heated to obtain a complete solution. Filtered through celite to remove catalyst and washed through with 1:1 aq IMS. The filtrate and washings are concentrated in vacuo to ca 10 vols, and treated with cHCl (1 vol). Reconcentrated in vacuo to ca 4 vols, by which time a thick slurry results. This is collected by vacuum filtration and washed with water and dried at 50C in vacuo to constant weight. Yield is 70-75% as hydrochloride salt.

Compound (VIII) is prepared from (IX) or may be commercially obtained.

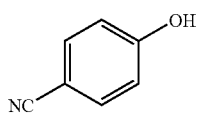
(IX)

(IX) is commercially available.

Preferably the compound is obtained as the parent and forms 2 and 6 are particularly preferred polymorphs. Water must be removed prior to crystallisation to obtain the parent and either form 2 or 6 can be obtained as described hereinbelow. Form 2 and form 6 can be obained from a variety of crystallisation solvents. Typically both can be obtained from ethyl acetate/iso-octane mixtures by seeding after the final hydrolysis reaction.

Forms 2 and 6 form a further feature of the invention and may be prepared by the method of this invention or any other method apparent to a person skilled in the art.

As detailed above, the compounds of the invention find utility in the hPPAR alpha mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, and regulation of appetite and food intake in subjects suffering from disorders such as obesity, anorexia bulimia, and anorexia nervosa. Other diseases or conditions include inflammation. In particular, the compounds of this invention are useful in the treatment and prevention of cardiovascular diseases and conditions including atherosclerosis, arteriosclerosis, hypertriglyceridemia, and mixed dyslipidaemia.

It will also be appreciated by those skilled in the art that the compounds of the present invention may also be utilized in the form of a pharmaceutically acceptable salt or solvate thereof. The physiologically acceptable salts of the compounds of formula (I) include conventional salts formed from pharmaceutically acceptable inorganic or organic acids or bases. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both the compound of the invention and its pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising at least one of the compounds of the invention or pharmaceutically acceptable salts or solvates thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compound of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compound may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The compound of the invention for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma agonists (for example thiazolidinediones such as e.g. Pioglitazone and Rosiglitazone). The compounds may also be used in combination with antihypertensive agents such as calcium channel antagonists and ACE inhibitors. The invention thus provides in a further aspect the use of a combination comprising a compound of formula (I) with a further therapeutic agent in the treatment of a hPPAR alpha mediated disease.

When the compound of the invention is used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of the invention is used in combination with a second therapeutic agent active against the same hPPAR alpha mediated disease, the dose of each compound may differ from that when the compound is used alone. Appropriate doses will be readily appreciated by those skilled in the art.

The invention is illustrated by reference to the following Examples which should not be construed as limiting thereto.

EXAMPLES

1. Preparation of Form 2

2-methyl-2[4-{[4-methyl-2-[4-trifluoromethyl thiazol-5-yl-carbonyl amino]methyl}phenoxy propionic acid was dissolved in 3 vol ethyl acetate and warmed to 60° C. Iso-octane (3 vols) was then added over 20 mins, then the batch was seeded with authentic material (0.001 wt, Form 2). Further iso-octane (3 vols) was added over 30 mins, causing the batch to crystallise. The mixture was allowed to stir at 62° C. for 60±min, before being cooled back to 2° C. over 60 min. Aged at this period for a further 60 min, then the product was collected by vacuum filtration, and washed sequentially with 3:1 iso-octane:ethyl acetate, (1 vol) and then with iso-octane (1 vol). Expected Yield: 93% theory, 90% w/w.

Alternatively, 2-methyl-2[4-{[4-methyl-2-[4-trifluoromethyl thiazol-5-yl-carbonyl amino]methyl}phenoxy propionic acid is dissolved in 3 vol of ethyl acetate by heating nearly to reflux. Iso-octane (5 vol) is added to the solution which is cooled to and held at 65° C. for 4 hrs. The resultant slurry is cooled to room temperature, held for an hour. The crystalline solid was collected by filtration and dried under vacuum to give the compound as crystalline form 2.

Alternatively, 2-methyl-2[4-{[4-methyl-2-[4-trifluoromethyl thiazol-5-yl-carbonyl amino]methyl}phenoxy propionic acid is dissolved in toluene (1.5 vol.) at reflux. After a hot filtration, the solution is slowly cooled to room temperature. The crystalline solid was collected by filtration, washed with toluene and dried under vacuum to give the compound as crystalline form 2.

Form 2 can be unambiguously defined by:
XRD diagram: (FIG. 1)
Sample preparation: Powder placed on a sample holder in silica
X-ray tube voltage (kv), current (mA): 40 kV, 40 mA
Temperature/humidity: Ambient
Chopper: 0.03 Deg
Scan mode rate: Continuous, 1 Deg 2 teta/min
Sample spinner: On.
Divergent slit incident bean: V12
Scatter slit incident, scatter lit diffracted: 2 mm, 0.1 mm
Receiving slit: 0.6 mm
Scan range: 5 to 45 2 teta.
Form 2
2theta, d-spacing
4.6, 19
8.6, 10
9.2, 9.6
11.7, 7.6
13.7, 6.4
14.5, 6.1
15.5, 5.7
17.1, 5.2
18.3, 4.8
18.9, 4.7
19.7, 4.5
20.0, 4.4
20.7, 4.3
21.6, 4.1
22.7, 3.9
22.9, 3.9
25.4, 3.5
27.6, 3.2
32.3, 2.8
37.1, 2.4
41.9, 2.1

Figure 2:
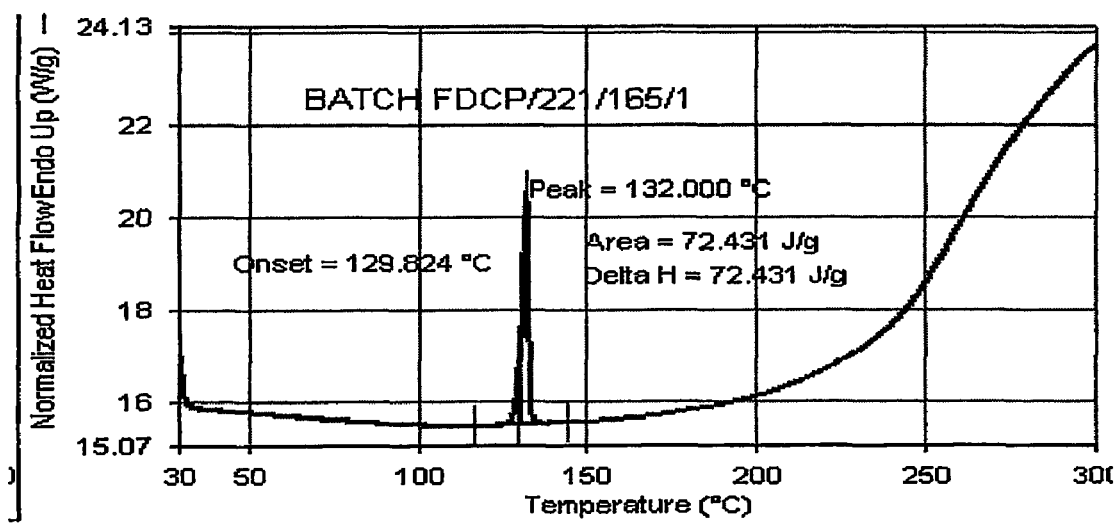
FIG. 2: DSC diagram of form 2 of 2-methyl-2-[4-{[4-methyl-2-[4-trifluoromethylphenyl]thiazol-5-yl-carbonyl) amino]methyl}phenoxy]propionic acid.

DSC (FIG. 2)
DSC:
Temperature Ramp: 10° C./min
Start, Stop temperature: 10 to 300° C.
Purge Gas,Rate: $N_2$ 50 mL/min
Pan: 30 µl aluminium vented.
Form 6

Form 2 (1 g) was dissolved in EtOAc (5 ml, 5 vol). The solution was stirred at RT and within an hour it had become a suspension. The solid form 6 was isolated by filtration.

In an alternative method, 2-methyl-2[4-{[4-methyl-2-[4-trifluoromethyl thiazol-5-yl-carbonyl amino]methyl}phenoxy propionic acid was dissolved in 3 vol of ethyl acetate by heating to reflux and adjusted to 20±3° C. The batch was then seeded with authentic material (0.001 wt, Form 6), and allowed to stir for 30-60 mins until crystallisation was well established. Iso-octane (3 vols) was added over 30 mins, and the mixture was allowed to stir at 20° C. for 60 min, before being cooled to 2° C. over 30 min. Aged at this period for a minimum of 60 min, then the product was collected by vacuum filtration, and washed sequentially with 1:1 iso-octane:ethyl acetate, (1 vol) and then with iso-octane (1 vol). Expected Yield: 93% theory, 90% w/w.

Figure 3:
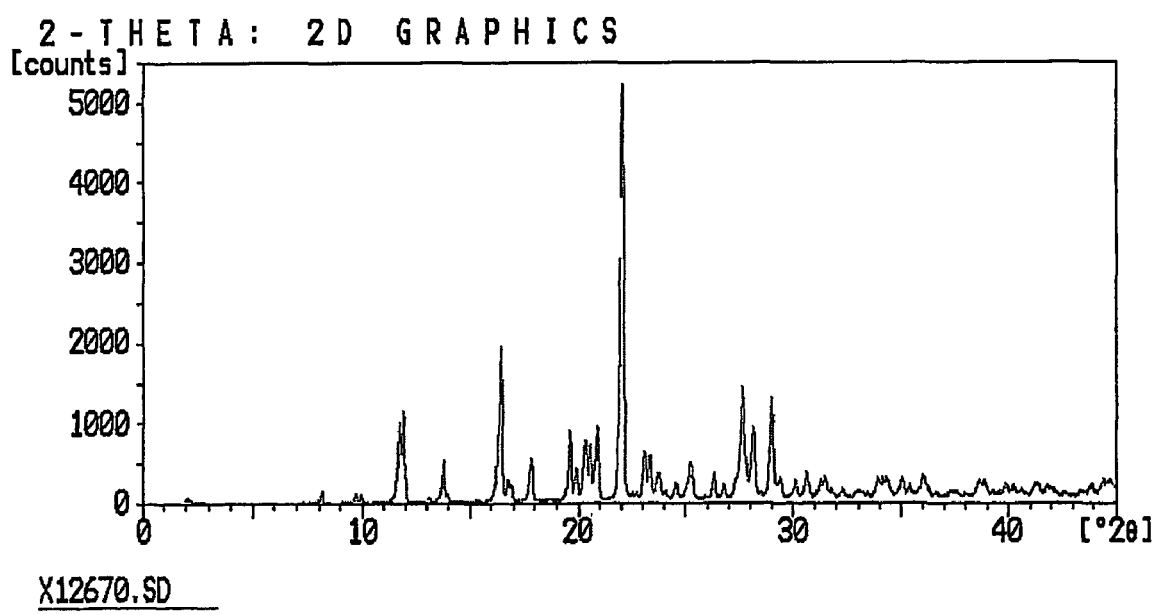
FIG. 3: XRD diagram of form 6 of 2-methyl-2-[4{[4-methyl-2-[4-trifluoromethylphenyl]thiazol-5-yl-carbonyl) amino]methyl}phenoxy]propionic acid.

Form 6 can be unambiguously defined by XRPD (FIG. 3)

Figure 4:
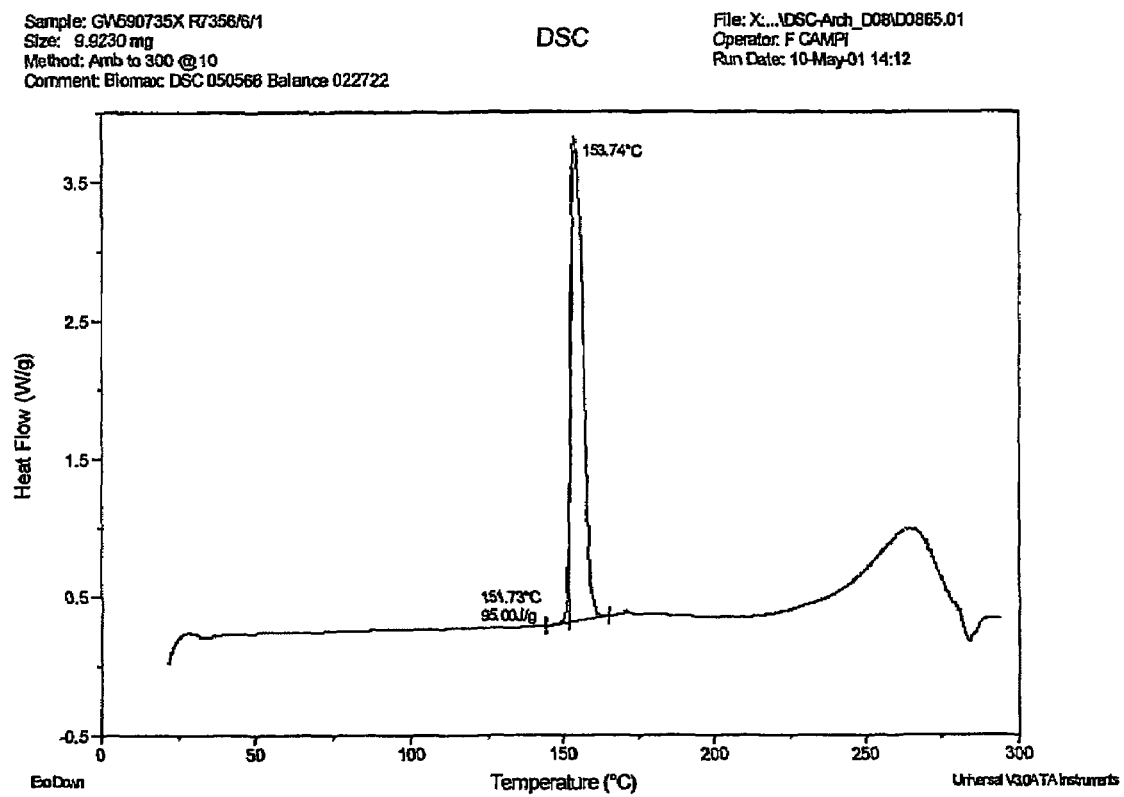
FIG. 4: DSC diagram of form 6 of 2-methyl-2-[4-{[4-methyl-2-[4-trifluoromethylphenyl]thiazol-5-yl-carbonyl) amino]methyl}phenoxy]propionic acid.

Sample preparation: powder packed on a front filled recessed silica holder.
X-ray tube voltage: 40 kV
X-ray tube current: 55 mA
Temperature/humidity: ambient
Wavelength Alpha1: 1.54 Å
Start angle: 2° 2θ
End angle: 45° 2θ
Step size: 0.02° 2θ
Time per step: 1.0 second Diffractometer:
  Sample spinner: ON
Primary Optics:
  Soller slit: 0.04 rad
  Divergence slit: automatic
  Irradiated length: 10.0 mm
Secondary Optics:
  Receiving slit: 0.20 mm
  Soller slit: 0.04 rad
  Form 6
2theta, d-spacing
11.7, 7.5
11.9, 7.4
13.8, 6.4
16.5, 5.4
17.9, 5.0
19.6, 4.5
20.5, 4.4
20.6, 4.3
20.9, 4.2
22.1, 4.0
23.1, 3.9
23.4, 3.8
27.7, 3.2
28.2, 3.2
29.0, 3.1
DSC—(FIG. 4).

The invention claimed is:

1. A method of preparing a compound of formula (I)

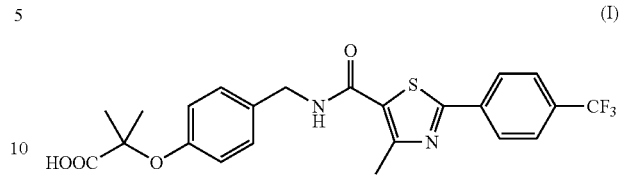

(I)

and pharmaceutically acceptable salts and solvates thereof comprising the reaction of a compound of formula (II)

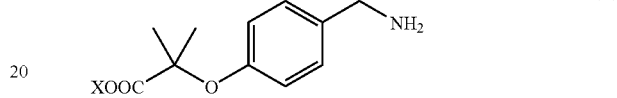

(II)

wherein X is Me or H with a compound of formula (III)

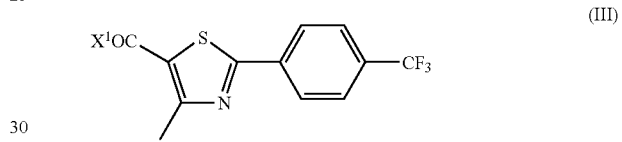

(III)

wherein $X^1$ is chlorine or imidazole.

* * * * *